United States Patent [19]  [11] 4,121,037
Nakamura et al.  [45] Oct. 17, 1978

[54] PROCESS FOR PRODUCING 5-FLUOROURACIL DERIVATIVE WITH A CALCIUM CHLORIDE CATALYST

[75] Inventors: Toshio Nakamura, Ohmiya; Yasuo Hoshide, Tokyo; Yoshio Hashimoto, Gyoda; Kenichi Suzuki, Saitama; Yohji Yoshida, Kawaguchi, all of Japan

[73] Assignee: Nikken Chemicals Co., Ltd., Tokyo, Japan

[21] Appl. No.: 774,050

[22] Filed: Mar. 3, 1977

[30] Foreign Application Priority Data

Jun. 26, 1976 [JP] Japan .................................. 51-75713
Aug. 28, 1976 [JP] Japan ................................ 51-102800

[51] Int. Cl.² ........................................ C07D 239/54
[52] U.S. Cl. .................................................. 544/313
[58] Field of Search ...................................... 260/260

[56] References Cited

U.S. PATENT DOCUMENTS 4,039,546  8/1977  Giller et al. .......................... 260/260

OTHER PUBLICATIONS

Ozaki et al., Chem. Abstracts, vol. 85, (1976), 192753x.

Brossmer et al., Chem. Abstracts, vol. 78, (1973), 58343r.

Primary Examiner—Paul M. Coughlan, Jr.
Attorney, Agent, or Firm—Oblon, Fisher, Spivak, McClelland & Maier

[57] ABSTRACT

5-Fluorouracil derivative having the formula

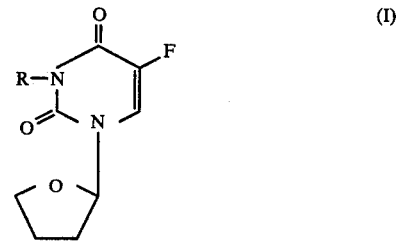

wherein R represents hydrogen atom or 2-tetrahydrofuryl group is produced by reacting more than equi-mole of 2,3-dihydrofuran with 5-fluorouracil in a polar aprotic solvent with a catalytically effective amount of a catalyst selected from the group consisting of metal halides, non-metal halides, tertiary amine salt of inorganic acids and organic acids in neutral or basic condition at 50° to 150° C under pressure.

14 Claims, No Drawings

PROCESS FOR PRODUCING 5-FLUOROURACIL DERIVATIVE WITH A CALCIUM CHLORIDE CATALYST

BACKGROUND OF THE INVENTION

1. Field of the Invention

The present invention relates to a process for producing 5-fluorouracil derivative having the formula

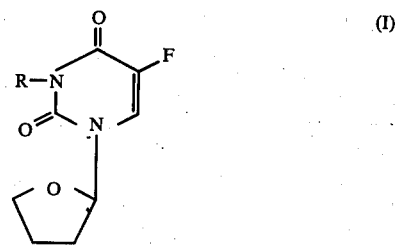

wherein R represents hydrogen atom and 2-tetrahydrofuryl group.

2. Description of the Prior Art

The 5-fluorouracil derivatives having the formula I, are useful as medicines and intermediates for medicines. Especially, the $N_1$(2-tetrahydrofuryl)-5-fluorouracil (R = H in formula I) has been known to be oral antineoplastic agent having low toxicity.

Heretofore, the following processes have been known to produce N-substituted-fluorouracils.

(1) The process for reacting mercury salt of 5-fluorouracil with 2-chlorotetrahydrofuran. (British Pat. No. 1,168,391 and Hiller et al.; Dokl Akad. Nauk. (USSR) 176[2]332, 1967).

(2) The process for reacting 2,4-bis(trimethylsilyl)-5-fluorouracil with 2-chlorotetrahydrofuran (British Pat. No. 1,168,391).

(3) The process for reacting 2,4-bis(trimethylsilyl)-5-fluorouracil with 2-acyloxytetrahydrofuran or 2-alkoxytetrahydrofuran. (Japanese Unexamined Patent Publication Nos. 50384/1975 and 105674/1975).

(4) The process for reacting 5-fluorouracil with an alkali metal hydride and then reacting the resulting alkali metal salt of 5-fluorouracil with 2-halogenotetrahydrofuran. (Japanese Unexamined Patent Publication No. 8282/1976).

However, in these conventional processes, the starting materials such as 2-chlorotetrahydrofuran which are easily decomposed and are produced by using stimulus gas are used and the yields are low.

In the other processes, 2-acyloxytetrahydrofuran or 2-alkoxytetrahydrofuran of which manufacture causes dangerous exothermic reaction is needed or the expensive raw material such as hexamethyldisilasane is needed.

Accordingly, from the viewpoint of cost or safety of the operation, these conventional processes are not satisfactory.

In Dokl, Akad, Nauk, (USSR), it is described that a condensed product could not be obtained by direct reaction of the substituted uracil with 2,3-dihydrofuran. In C.W. Noell et al.; J. Heterocyclic Chem. 3, 5, (1966), the similar fact is described.

Accordingly, it has been considered to be impossible to directly react 5-fluorouracil with 2,3-dihydrofuran.

However, the inventors have studied the reactivity of 5-halogeno-substituted uracils in detail, and have found that the reaction of 5-halogeno-substituted uracil with 2,3-dihydrofuran is surprisingly resulted in a polar aprotic solvent at higher than specific temperature under pressure. Moreover, the inventors have found that the reaction can be promoted with a catalyst.

SUMMARY OF THE INVENTION

It is an object of the present invention to provide a novel process for producing 5-fluorouracil derivatives by a direct reaction of 5-fluorouracil with 2,3-dihydrofuran without the above-mentioned disadvantages.

The other object of the present invention is to provide an improved process for producing 5-fluorouracil derivatives with economical advantages.

The other objects of the invention will be understood from the following description.

The objects of the present invention have been attained by producing 5-fluorouracil derivative having the formula (I) by reacting 5-fluorouracil with more than equi-mole of 2,3-dihydrofuran in a polar aprotic solvent with a catalytically effective amount of a catalyst selected from the group consisting of metal halides, non-metal halides, inorganic acids and organic acids in neutral or basic condition if necessary with a tertiary amine at 50° to 150° C under pressure in a sealed reactor for enough reaction time such as 0.5 to 50 hours.

DETAILED DESCRIPTION OF THE PREFERRED EMBODIMENTS

The polar aprotic solvents used in the process of the invention are preferably the solvents dissolving both of 5-fluorouracil and 2,3-dihydrofuran from the viewpoint of the operation for the reaction.

Suitable polar aprotic solvents include amides such as N,N-dimethylformamide, N,N-dimethylacetamide, tetramethyl urea, hexamethyl phosphoramide; tertiary amines such as trialkyl amines such as triethylamine; substituted morpholine such as N-methyl morpholine; substituted or nonsubstituted pyridines such as pyridine, α-picoline, β-picoline, γ-picoline, lutidine; and quinoline, isoquinoline, pyrimidine, pyrazine, N,N-dimethylaniline, etc..

It is preferable to use N,N-dimethylformamide, N,N-dimethylacetamide, pyridine, α-picoline, β-picoline, γ-picoline, etc..

The catalysts used in the process of the invention can be alkali metal halides, alkaline earth metal halides, Lewis acids of metal or non-metal halides, or inorganic acids or organic acids. The catalysts are classified depending upon the characteristics as follows:

GROUP A

Alkali metal halides and alkaline earth metal halides calcium halides such as calcium chloride, calcium bromide, calcium iodide;

magnesium halides such as magnesium chloride, magnesium bromide, magnesium iodide;

strontium halides such as strontium chloride, strontium bromide, strontium iodide;

barium halides such as barium chloride, barium bromide, barium iodide;

alkali metal halides such as lithium chloride, sodium chloride, potassium chloride, lithium bromide, lithium iodide, potassium bromide, potassium iodide, sodium bromide.

GROUP B

(a) Metal halides except alkali metal and alkaline earth metal halides iron halides such as ferrous chloride, ferric chloride; aluminum halides such as aluminum chloride; zinc halide such as zinc chloride; tin halides such as stannous chloride, stannic chloride, stannous bromide, stannic bromide; copper halides such as cuprous chloride, cuprous bromide, cuprous iodide, cupric chloride; antimony halides such as antimony chloride; manganese halides such as manganese chloride; chromium halides such as chromium chloride; nickel halide such as nickel chloride; cobalt halides such as cobalt chloride; lead halides such as lead chloride; titanium halide such as titanium tetrachloride; cadmium halides such as cadmium chloride, cadmium iodide; selenium halide such as selenium chloride; mercury halides such as mercurous chloride, mercuric chloride, etc..

(b) Non-metal halides silicon tetrachloride; phosphorous halides such as phosphorus trichloride, phosphorus pentachloride, phosphorus oxychloride; boron halide such as boron trichloride, boron trifluoride and complexes thereof with ether, methanol, etc..

(c) Organic acids and inorganic acids p-toluenesulfonic acid, benzoic acid, trifluoroacetic acid, hydroquinone, phosphoric acid, phosphorus pentoxide, hydrochloric acid, sulfuric acid.

In the catalysts of Group A, the optimum catalysts are lithium chloride, sodium chloride, potassium chloride, magnesium chloride, calcium chloride, strontium chloride, barium chloride, calcium bromide, potassium iodide, sodium bromide, etc..

In the catalysts of Group B, the optimum catalysts are antimony trichloride, boron trifluoride-etherate, stannic chloride, stannous chloride, ferric chloride, ferrous chloride, cuprous bromide, zinc chloride, cadmium iodide, aluminum chloride, phosphoric acid, phosphorus pentoxide, p-toluenesulfonic acid, etc..

In the process of the invention, the reaction is carried out at a ratio of more than equi-mole usually 1 to 10 mole preferably 2 to 6 mole of 2,3-dihydrofuran per 1 mole of 5-fluorouracil and 0.0001 to 5 mole preferably 0.001 to 1 mole of the catalyst per 1 mole of 5-fluorouracil.

When an amide type solvent is used, 0.001 to large excess of a weak basic compound is used depending upon the kind and amount of the catalyst.

In this case, it is preferable to use the weak basic compound at a ratio of more than that of the catalyst so as to adjust the reaction system to be neutral to basic condition.

The reaction is carried out at 50° to 150° C preferably 90° to 150° C especially 100° to 130° C.

The reaction time is dependent upon the kind and amount of the catalyst and the solvent, and the reaction temperature, and is usually in a range of 30 minutes to 50 hours preferably 2 to 24 hours.

In the process of the invention, 2,3-dihydrofuran has a boiling point of 54.5° C and it is vaporized at the reaction temperature. The reaction is carried out under pressure preferably an autovaporized pressure of higher in an autoclave or a sealed tube.

The optimum embodiments of the process of the invention will be illustrated.

In an autoclave, 5-fluorouracil and 2,3-dihydrofuran at a ratio of 1 to 10 mole especially 2 to 6 mole per 1 mole of 5-fluorouracil, and a polar aprotic solvent of pyridine, α-picoline, β-picoline, γ-picoline, lutidine, pyrimidine or pyradine especially pyridine, α-picoline, β-picoline or γ-picoline are charged.

Then, the catalyst of Group A or Group B especially lithium chloride, sodium chloride, potassium chloride, sodium bromide, potassium iodie, magnesium chloride, calcium chloride, strontium chloride, barium chloride, calcium bromide, calcium iodide, ferrous chloride, ferric chloride, cuprous chloride, cuprous bromide, cuprous iodide, zinc chloride, cadmium iodide, aluminum chloride, boron trifluoride-complex, stannous chloride, stannic chloride, antimony trichloride, phosphoric acid, phosphorus pentoxide or p-toluenesulfonate, is added to the mixture at a ratio of 0.0001 to 5 mole especially 0.001 to 1 mole per 1 mole of 5-fluorouracil. The mixture is heated at 50° to 150° C preferably 90° to 150° C especially 100° to 130° C for 0.5 to 50 hours especially 2 to 24 hours under an autovaporized pressure.

The other optimum embodiments of the process of the invention will be illustrated.

In an autoclave, 5-fluorouracil and 2,3-dihydrofuran at a ratio of 1 to 10 mole especially 2 to 6 mole per 1 mole of 5-fluorouracil, and a polar aprotic solvent of N,N-dimethylformamide, N,N-dimetylacetamide, tetramethyl urea or hexamethylphosphoramide, especially N,N-dimethylformamide or N,N-dimethylacetamide, are charged.

Then, the catalyst of Group A especially lithium chloride, sodium chloride, potassium chloride, sodium bromide, potassium iodide, magnesium chloride, calcium chloride, strontium chloride, barium chloride, calcium bromide or calcium iodide is added to the mixture at a ratio of 0.0001 to 5 mole especially 0.001 to 1 mole per 1 mole of 5-fluorouracil.

The mixture is heated at 50° to 150° C preferably 90° to 150° C especially 100° to 130° C for 0.5 to 50 hours especially 2 to 24 hours under an autovaporized pressure.

The other optimum embodiments of the process of the invention will be illustrated.

In an autoclave, 5-fluorouracil and 2,3-dihydrofuran at a ratio of 1 to 10 mole preferably 2 to 6 mole per 1 mole of 5-fluorouracil, and a polar aprotic solvent of N,N-dimethylformamide, N,N-dimethylacetamide, tetramethyl urea or hexamethyl phosphoramide especially N,N-dimethylformamide or N,N-dimethylacetamide, are charged.

Then, the catalyst of Group B especially, ferrous chloride, ferric chloride, cuprous chloride, cuprous bromide, cuprous iodide, zinc chloride, cadmium iodide, aluminum chloride, boron trifluoridecomplex, stannous chloride, stannic chloride, antimony trichloride, phosphoric acid, phosphorus pentoxide or p-toluenesulfonic acid is added to the mixture at a ratio of 0.0001 to 5 mole especially 0.001 to 1 mole per 1 mole of 5-fluorouracil.

A weak basic compound especially an amine such as triethylamine, pyridine, α-picoline, β-picoline, γ-picoline, lutidine, pyradine, pyrimidine, quinoline, isoquinoline, N-methyl morphorine, or N,N-dimethylaniline, is added to adjust pH to neutral to basic condition.

The mixture is heated at 50° to 150° C preferably 90° to 150° C especially 100° to 130° C for 0.5 to 50 hours especially 2 to 24 hours under an autovaporized pressure.

In accordance with the process of the invention, $N_1,N_3$-bis(2-tetrahydrofuryl)-5-fluorouracil (R = 2-tetrahydrofuryl in formula I) is treated in an inert solvent in the presence of an acid at the room temperature for a short time (longer than 5 min. preferably longer than 15 min.) to easily convert it into $N_1$-(2-tetrahydrofuryl)-5-fluorouracil.

Suitable inert solvents include toluene, benzene, dichloromethane, methanol, ethanol, etc..

Suitable acids include inorganic acids such as hydrogen chloride, sulfuric acid, phosphoric acid, and organic acids such as acetic acid, trifluoroacetic acid; p-toluenesulfonic acid, etc.. It is preferable to use hydrogen chloride, acetic acid, trifluoroacetic acid.

The inert solvents should be inert to 5-fluorouracil derivatives.

It is possible to carry out the acid treatment to the reaction mixture without separating $N_1,N_3$-bis(2-tetrahydrofuryl)-5-fluorouracil from the reaction mixture.

In order to separate $N_1$-(2-tetrahydrofuryl)-5-fluorouracil and $N_1,N_3$-bis(2-tetrahydrofuryl)-5-fluorouracil, it is possible to easily attain the purpose by the known methods such as a solvent extraction, a crystallization, and a column chromatography and a combination thereof.

In accordance with the process of the invention, the steps for producing 5-fluorouracil derivative especially $N_1$-(2-tetrahydrofuryl)-5-fluorouracil can be remarkably shorten and economical raw materials can be used and the reaction conditions are relatively mild and the yield is remarkably high and the cost of the production can be remarkably reduced, advantageously.

The invention will be further illustrated by certain examples.

EXAMPLE 1

In a sealed tube, 780 mg (6 m mole) of 5-fluorouracil, 5 ml of pyridine, 100 mg (0.90 m mole) of calcium chloride and 1.26 g (18 m mole) of 2,3-dihydrofuran were heated at 100° C for 3 hours. The reaction mixture further admixed with 800 mg (11.5 m mole) of 2,3-dihydrofuran and the mixture was heated for 17 hours. After the reaction, the insoluble matters in the reaction mixture were separated by a filtration. Pyridine was distilled off from the filtrate under a reduced pressure. The residue was dissolved in chloroform and a small amount of the insoluble matter was separated by a filtration.

Chloroform was distilled off from the filtrate and the residue was purified by a column chromatography using a silica gel column (mixture of chloroform and acetone = 8 : 1 (V/V) as a developing medium) to obtain 1.11 g of $N_1,N_3$-bis(2-tetrahydrofuryl)-5-fluorouracil (yield: 68.5%) and 2.83 g of $N_1$-(2-tetrahydofuryl)-5-fluorouracil (yield: 23.6%).

The former product was recrystallized from ether to obtain a purified product having a melting point of 99° to 101° C.

NMR $\tau$(CDCl$_3$, TMS, 60 Mz)
4.04 (1H), 3.35 (1H),
2.93 (1Hd, J=7Hz).

The latter product was recrystallized from ethanol to obtain a purified product having a melting point of 166° to 168° C.

Elementary Analysis ($C_8H_9N_2O_3F$)

|  | C | H | N |
|---|---|---|---|
| Calculated | 48.00% | 4.53% | 13.99% |
| Found | 48.12% | 4.65% | 14.18% |

NMR $\tau$(CDCl$_3$, TMS, 60 Mz)
3.98 (1H), 2.72 (1 Hd, J = 7Hz)
−0.15 (1H).

EXAMPLES 2 TO 4

In accordance with the process of Example 1 except using potassium iodide, zinc chloride or cadmium iodide instead of calcium chloride, the reaction of 5-fluorouracil with 2,3-dihydrofuran was carried out. The results are shown in Table 1.

Table 1

| Example | Catalyst | $N_1$-(2-tetrahydrofuryl)-5-fluorouracil (yield) | $N_1, N_3$-bis(2-tetrahydrofuryl)-5-fluorouracil (yield) |
|---|---|---|---|
| 2 | KI 100 mg (0.60 m mole) | 422 mg (35.2%) | 1,020 mg (63.2%) |
| 3 | ZnCl$_2$ 100 mg (0.73 m mole) | 493 mg (41.1%) | 180 mg (11.1%) |
| 4 | CdI$_2$ 100 mg (0.27 m mole) | 324 mg (27.0%) | 426 mg (26.3%) |

EXAMPLE 5

In a sealed tube, 780 mg (6 m mole) of 5-fluorouracil, 5 ml of pyridine, 100 mg (0.44 m mole) of antimony trichloride and 1.26 g (18 m mole) of 2,3-dihydrofuran were heated at 100° C for 3 hours. The reaction mixture was further admixed with 800 mg (11.5 m mole) of 2,3-dihydrofuran and the mixture was heated for 17 hours. After the reaction, pyridine was distilled off under a reduced pressure and the residue was dissolved in chloroform and the insoluble matters were separated by a filtration. Chloroform was distilled off from the filtrate and the residue was purified by a column chromatography using a silica gel column (mixture of chloroform and acetone = 8 : 1 (V/V) as a developing medium) to obtain 1.10 g of $N_1,N_3$-bis(2-tetrahydrofuryl)-5-fluorouracil (yield: 68.0%) and 325 mg of $N_1$-(2-tetrahydrofuryl)-5-fluorouracil (yield: 27%).

The former product was recrystallized from ether to obtain a purified product having a melting point of 99° to 101° C. The latter product was recrystallized from ethanol to obtain a purified product having a melting point of 166° to 168° C.

EXAMPLES 6 to 9

In accordance with the process of Example 5 except using boron trifluoride-etherate, ferric chloride, ferrous chloride or phosphoric acid instead of antimony chloride, the reaction of 5-fluorouracil with 2,3-dihydrofuran was carried out. The results are shown in Table 2.

Table 2

| Example | Catalyst | $N_1$-(2-tetrahydrofuryl)-5-fluorouracil (yield) | $N_1, N_3$-bis (2-tetrahydrofuryl)-5-fluorouracil (yield) | Note |
|---|---|---|---|---|
| 6 | BF$_3$-ether 100 mg | 545 mg (45.4%) | 776 mg (47.9%) | |

Table 2-continued

| Example | Catalyst | $N_1$-(2-tetra-hydrofuryl)-5-fluorouracil (yield) | $N_1, N_3$-bis(2-tetrahydrofuryl)-5-fluorouracil (yield) | Note |
|---|---|---|---|---|
| 7 | $FeCl_3 \cdot 6H_2O$ 100 mg (0.37 m mole) | 682.5 mg (56.9%) | 340.2 mg (21.0%) | * |
| 8 | $FeCl_2$ 100 mg | 588 mg (49.0%) | 388.8 mg (24.0%) | ** |
| 9 | phosphoric acid 100 mg (1.02 m mole) | 355 mg (29.6%) | 1,090 mg (67.3%) | |

Note:
*10 ml of solvent
**10 ml of solvent

EXAMPLE 10

In a sealed tube, 780 mg (6 m mole) of 5-fluorouracil, 5 ml of pyridine, 100 mg (0.70 m mole) of phosphorus pentoxide and 1.26 g (18 m mole) of 2,3-dihydrofuran were heated at 100° C for 17 hours. After the reaction, pyridine was distilled off from the reaction mixture under a reduced pressure. The residue was dissolved in chloroform and the insoluble unreacted 5-fluorouracil was separated by a filtration and the residue was purified by a column chromatography using a silica gel column (mixture of benzene; ethyl acetate and acetone = 2 : 1 : 1 (V/V) as a developing medium) to obtained 200 mg of $N_1,N_3$-bis(2-tetrahydrofuryl)-5-fluorouracil (yield: 12.3%) and 757.6 mg of $N_1$-(2-tetrahydrofuryl)-5-fluorouracil (yield: 63.0%).

The former product was recrystallized from ether to obtain a purified product having a melting point of 99° to 101° C. The latter product was recrystallized from ethanol to obtain a purified product having a melting point of 166° to 168° C.

EXAMPLES 11 to 13

In accordance with the process of Example 10 except using cuprous bromide, aluminum chloride or p-toluenesulfonic acid instead of phosphorus pentoxide, the reaction of 5-fluorouracil with 2,3-dihydrofuran was carried out. The results are shown in Table 3.

Table 3

| Example | Catalyst | $N_1$-(2-tetrahydrofuryl)-5-fluorouracil (yield) | $N_1, N_3$-bis(2-tetrahydrofuryl)-5-fluorouracil (yield) | Note |
|---|---|---|---|---|
| 11 | CuBr 100 mg (0.70 m mole) | 600 mg (50.0%) | 100 mg (6.2%) | * |
| 12 | $AlCl_3$ 100 mg (0.75 m mole) | 305 mg (25.4%) | 103 mg (6.4%) | ** |
| 13 | p-toluene-sulfonic acid 103 mg (0.6 m mole) | 511 mg (42.6%) | — | *** |

Note:
*reaction time: 20 hours developing medium chloroform : acetone = 8 : 1 V/V.
**reaction time: 3 hours developing medium chloroform : acetone = 8 : 1 V/V.
***reaction time: 7 hours developing medium ethyl acetate : benzene = 5 : 1 V/V.

EXAMPLE 14

In accordance with the process of Example 1 except using 100 mg (0.38 m mole) of stannic chloride instead of calcium chloride, the reaction of 5-fluorouracil with 2,3-dihydrofuran was carried out. After the reaction, the insoluble matters in the reaction mixture were separated by a filtration. Pyridine was distilled off from the filtrate under a reduced pressure.

The residue was dissolved in chloroform and the insoluble matters (small amount) were separated by a filtration. Chloroform was distilled off from the filtrate and benzene was added to the residue and the precipitated crystals were separated by a filtration to obtain 150 mg of $N_1$-(2-tetrahydrofuryl)-5-fluorouracil. (yield: 12.5%).

The product was recrystallized from ethanol to obtain a pure compound having a melting point of 166° to 168° C.

A mixture of benzene and trifluoroacetic acid was added to the mother liquor to make the ratio of benzene and trifluoroacetic acid is 2:1 (V/V).

The mixture was stirred for 15 minutes at the room temperature and the solvent was distilled off under a reduced pressure and the residue was recrystallized from a mixture of ethanol and ether to obtain 750 mg of $N_1$-(2-tetrahydrofuryl)-5-fluorouracil. (yield: 62.5%). The product was recrystallized from ethanol to obtain a pure compound having a melting point of 166° to 168° C.

EXAMPLE 15

In accordance with the process of Example 5 except using 100 mg of stannous chloride instead of antimony trichloride, the reaction of 5-fluorouracil with 2,3-dihydrofuran was carried out.

Pyridine was distilled off from the reaction mixture under a reduced pressure and the residue was dissolved in chloroform and the insoluble matters (small amount) were separated by a filtration and chloroform was distilled off and the resulting crystals were washed with ether to obtain 919 mg of $N_1$-(2-tetrahydrofuryl)-5-fluorouracil. (yield: 76.6%). The product was recrystallized from ethanol to obtain a pure compound having a melting point of 166° to 168° C.

Ether was distilled off from the ether wash liquid and 4 ml of benzene and 2 ml of trifluoroacetic acid were added to the residue, and the mixture was stirred at the room temperature for 15 minutes and benzene and trifluoroacetic acid were distilled off, and the residue was washed with ether to obtain 249 mg of $N_1$-(2-tetrahydrofuryl)-5-fluorouracil. (yield: 20.7%).

The product was recrystallized from ethanol to obtain a pure compound having a melting point of 166° to 168° C.

EXAMPLE 16

In 2.5 liter autoclave, 300 g (2.31 mole) of 5-fluorouracil, 720 ml of pyridine, 1.84 g (0.017 mole) of fine powdery calcium chloride and 485 g (6.93 mole) of 2,3-dihydrofuran were charged, and the autoclave was shaken at 105° to 110° C for 6.5 hours. After the reaction, the insoluble matters in the reaction mixture were separated by a filtration. Pyridine was distilled off from the filtrate under a reduced pressure. The residue was admixed with 700 ml of toluene and 150 ml of trifluoroacetic acid and the mixture was stirred at the room temperature for one night and then toluene and trifluoroacetic acid were distilled off under a reduced pressure and the residue was washed with ether to obtain 430 g of white crystals of $N_1$-(2-tetrahydrofuryl)-5-fluorouracil. (yield: 93.2%; melting point: 157° to 160° C).

The product was recrystallized from ethanol to obtain 360 g of a pure compound having a melting point of 166° to 168° C. The object product was purified from the mother liquor to obtain 35.6 g of the pure compound having a melting point of 166° to 168° C.

EXAMPLE 17

In 200 ml autoclave, 26.0 g of 5-fluorouracil (200 m mole), 60 ml of pyridine, 160 mg (1.44 m mole) of fine powdery calcium chloride and 28.0 g (400 m mole) of 2,3-dihydrofuran were charged and the autoclave was shaken at 105° to 110° C for 6.5 hours.

After the reaction, the insoluble matters in the reaction mixture were separated by a filtration. Pyridine was distilled off from a filtrate under a reduced pressure. The residue was dissolved in chloroform and the insoluble unreacted 5-fluorouracil (0.24 g) was separated by a filtration.

Chloroform was distilled off, and the residue was admixed with 130 ml of toluene and 10 ml of trifluoroacetic acid, and the mixture was stirred at the room temperature for one night and toluene and trifluoroacetic acid were distilled off and the residue was washed with ether to obtain 33.5 g of white crystals of $N_1$-(2-tetrahydrofuryl)-5-fluorouracil. (yield: 83.8%; melting point: 157.5° to 160° C). The product was recrystallized from ethanol to obtain 30 g of a pure compound having a melting point of 166° to 168° C.

EXAMPLE 18

In a sealed tube, 780 mg (6 m mole) of 5-fluorouracil, 100 mg (0.90 m mole) of calcium chloride, 5 ml of N,N-dimethylformamide and 1.26 g (18 m mole) of 2,3-dihydrofuran were heated at 100° C for 3 hours.

The reaction mixture was further admixed with 800 mg (11.5 m mole) of 2,3-dihydrofuran and the mixture was heated for 17 hours. After the reaction, N,N-dimethylformamide was distilled off from the reaction mixture under a reduced pressure.

The residue was dissolved in chloroform and the insoluble matters (small amount) were separated. Chloroform was distilled off from the filtrate and the residue was admixed with 5 ml of toluene and 0.9 ml of trifluoroacetic acid and the mixture was stirred at the room temperature for one night and toluene and trifluoroacetic acid was distilled off under a reduced pressure and the residue was washed with ether to obtain 1.0223 g of white crystals of $N_1$-(2-tetrahydrofuryl)-5-fluorouracil (yield: 85.2%; melting point: 155.5° to 158.5° C). The product was recrystallized from ethanol to obtain 0.915 g of a pure compound having a melting point of 166° to 168° C.

Elementary analysis: ($C_8H_9FN_2O_3$)

|  | C | H | N |
|---|---|---|---|
| Calculated (%) | 48.00 | 4.53 | 13.99 |
| Found (%) | 48.05 | 4.61 | 14.01 |

EXAMPLE 19

In a sealed tube, 780 mg (6 m mole) of 5-fluorouracil, 100 mg (0.42 m mole) of calcium bromide($CaBr_2.2H_2O$), 5 ml of N,N-dimethylformamide and 1.26 g (18 m mole) of 2,3-dihydrofuran were heated at 100° C for 3 hours. The reaction mixture was further admixed with 800 mg (11.5 m mole) of 2,3-dihydrofuran and the mixture was heated for 17 hours. After the reaction, N,N-dimethylformamide was distilled off from the reaction mixture under a reduced pressure. The residue was dissolved in chloroform and the insoluble matter (small amount) were separated by a filtration.

Chloroform was distilled off from the filtrate and the residue was purified by a column chromatography using a silica gel column (mixture of chloroform and acetone = 8:1 (V/V) as a developing medium) to obtain 440 mg of $N_1,N_3$-bis(2-tetrahdrofuryl)-5-fluorouracil (yield: 27.1%) and 750 mg of $N_1$-(2-tetrahydrofuryl)-5-fluorouracil (yield: 62.5%).

The former was recrystallized from ether to obtain a pure compound having a melting point of 99° to 101° C.

Elementary analysis: ($C_{12}H_{15}FN_2O_4$)

|  | C | H | N |
|---|---|---|---|
| Calculated (%) | 53.33 | 5.59 | 10.36 |
| Found (%) | 53.03 | 5.51 | 10.20 |

The latter product was recrystallized from ethanol to obtain a pure compound having a melting point of 166° to 168° C.

EXAMPLES 20 TO 24

In accordance with the process of Example 19 except using sodium chloride, potassium chloride, magnesium chloride, barium chloride or calcium iodide instead of calcium bromide, the reaction of 5-fluorouracil with 2,3-dihydrofuran was carried out.

The results are shown in Table 4.

Table 4

| Example | Catalyst | $N_1$-(2-tetrahydro-furyl)-5-fluoro-uracil (yield) | $N_1, N_3$-bis(2-tetrahydrofuryl)-5-fluorouracil (yield) |
|---|---|---|---|
| 20 | NaCl 100 mg (1.17 m mole) | 706 mg (58.8%) | 572 mg (35.3%) |
| 21 | KCl 100 mg (1.34 m mole) | 727 mg (60.6%) | 540 mg (33.3%) |
| 22 | $MgCl_2$ 100 mg (1.05 m mole) | 685 mg (57.1%) | 509 mg (31.4%) |
| 23 | $BaCl_2$ 100 mg (0.48 m mole) | 690 mg (57.5%) | 505 mg (31.2%) |
| 24 | $CaI_2$ 100 mg | 727 mg (60.6%) | 393 mg (24.2%) |

EXAMPLE 25

In 400 ml autoclave, 52.0 g of 5-fluorouracil (0.4 mole) 120 ml of pyridine, 300 mg (2.7 m mole) of fine powdery calcium chloride and 84.0 g (1.2 mole) of 2,3-dihydrofuran were charged and autoclave was shaken at 120° C for 3 hours.

After the reaction, the insoluble matters in the reaction mixture were separated by filtration. Pyridine was distilled off from a filtrate under a reduced pressure. The residue was dissolved in 56 ml of methanol, and added with 475 mg of HCl dissolved in 4 ml of methanol and stand for over night at room temperature (20°–30° C). After cooling, separated crystals were filtrated and washed with cooled ethanol. 71.96 g (yield: 90.0%) of white crystals $N_1$-(2-tetrahydrofuryl)-5-fluorouracil (m.p. 166°–168° C) were obtained.

What is claimed is:

1. A process for producing a 5-fluorouracil derivative having the formula

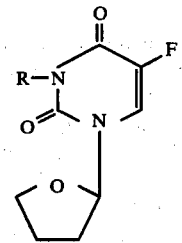

wherein R represents a hydrogen atom or a 2-tetrahydrofuryl group which comprises reacting more than an equimolar amount of 2,3-dihydrofuran with 5-fluorouracil in a polar aprotic solvent in the presence of a catalytically effective amount of calcium chloride as a catalyst under neutral or basic conditions at a reaction temperature of 50 to 150° C under at least autogenous pressure.

2. A process according to claim 1 which comprises reacting more than the stoichiometric amount of 2,3-dihydrofuran with 5-fluorouracil in a polar aprotic solvent in the presence of calcium chloride as a catalyst at a catalyst ratio of 0.0001 to 5 mole per 1 mole of 5-fluorouracil under neutral or basic conditions at a reaction temperature of 50° to 150° C under at least autogenous pressure for a reaction time of 0.5 to 50 hours.

3. A process according to claim 1 which comprises reacting 2,3-dihydrofuran at a ratio of 1 to 10 moles per 1 mole of 5-fluorouracil in a tertiary amine solvent in the presence of calcium chloride as a catalyst at a catalyst ratio of 0.0001 to 5 moles per 1 mole of 5-fluorouracil at a reaction temperature of 90° to 150° C for a reaction time of 1 to 50 hours under at least autogenous pressure.

4. A process according to claim 3, wherein the reaction temperature is within the range 100° to 130° C.

5. A process according to claim 3, wherein the tertiary amine solvent is pyridine, α-picoline, β-picoline, γ-picoline, lutidine, pyrimidine or pyrazine.

6. A process according to claim 3, wherein the ratio of 2,3-dihydrofuran is 2 to 6 moles per 1 mole of 5-fluorouracil, the catalyst ratio is 0.001 to 1 mole per 1 mole of 5-fluorouracil, the tertiary amine solvent is pyridine, α-picoline, β-picoline or γ-picoline, the reaction temperature is 100 to 130° C and the reaction time is 2 to 24 hours.

7. A process according to claim 1 which comprises reacting 2,3-dihydrofuran at a ratio of 1 to 10 moles per 1 mole of 5-fluorouracil in an amide solvent in the presence of calcium chloride as a catalyst at a catalyst ratio of 0.0001 to 1 mole per 1 mole of 5-fluorouracil at a reaction temperature of 90° to 150° C for a reaction time of 1 to 50 hours under at least autogenous pressure.

8. A process according to claim 7, wherein the reaction temperature is 100° to 130° C.

9. A process according to claim 8, wherein the amide solvent is N,N-dimethylformamide, N,N-dimethylacetamide, tetramethyl urea or hexamethylphosphoramide.

10. A process according to claim 7, wherein the reaction is carried out in the presence of an amine selected from the group consisting of triethylamine, N-methylmorphorine, pyridine, α-picoline, β-picoline, γ-picoline, lutidine, quinoline, isoquinoline, pyrimidine, pyrazine or N,N-dimethylaniline.

11. A process according to claim 7, wherein the ratio of 2,3-dihydrofuran is 2 to 6 moles per 1 mole of 5-fluorouracil, the catalyst ratio is 0.001 to 1 mole per 1 mole of 5-fluorouracil, the amide solvent is N,N-dimethylformamide or N,N-dimethylacetamide, the reaction temperature is 100° to 130° C and the reaction time is 2 to 24 hours.

12. A process according to claim 3, wherein the reaction mixture is treated in an inert solvent in the presence of an acid.

13. A process according to claim 7, wherein the reaction mixture is treated in an inert solvent in the presence of an acid.

14. A process according to claim 1, wherein $N_1,N_3$-bis(2-tetrahydrofuryl)-5-fluorouracil is separated from $N_1$-(2-tetrahydrofuryl)-5-fluorouracil and is treated in an inert solvent with an acid to convert it to $N_1$-(2-tetrahydrofuryl)-5-fluorouracil.